US00PP32643P2

(12) United States Plant Patent
Van Dijk

(10) Patent No.: US PP32,643 P2
(45) Date of Patent: Dec. 15, 2020

(54) ***ANTHURIUM* PLANT NAMED 'ANTHETAAD'**

(50) Latin Name: ***Anthurium andraeanum* L.**
Varietal Denomination: ANTHETAAD

(71) Applicant: ANTHURA B.V., Bleiswijk (NL)

(72) Inventor: Jan Van Dijk, Bleiswijk (NL)

(73) Assignee: Anthura B.V., Bleiswijk (NL)

( * ) Notice: Subject to any disclaimer, the term of this patent is extended or adjusted under 35 U.S.C. 154(b) by 0 days.

(21) Appl. No.: 16/873,257

(22) Filed: Mar. 5, 2020

(51) Int. Cl.
*A01H 5/02* (2018.01)
*A01H 6/10* (2018.01)

(52) U.S. Cl.
USPC ..... Plt./369

(58) Field of Classification Search
USPC ..... Plt./263.1, 365, 369
See application file for complete search history.

*Primary Examiner* — Susan McCormick Ewoldt
*Assistant Examiner* — Karen M Redden
(74) *Attorney, Agent, or Firm* — Jondle & Associates, P.C.

(57) ABSTRACT

A new *Anthurium* plant named 'ANTHETAAD' particularly distinguished by having shiny, blistered, red, oblong-cordate, and very durable spathes that retain the original color for a very long period of time, dark green and elliptical-cordate, durable leaves, white spadices with yellow tips, early and rich flowering continuously throughout the year, and a plant height of 40.0 cm to 45.0 cm is disclosed.

3 Drawing Sheets

Genus and species: *Anthurium andraeanum* L.
Variety denomination: 'ANTHETAAD'.

BACKGROUND OF THE NEW PLANT

The present invention comprises a new and distinct variety of *Anthurium*, botanically known as *Anthurium andraeanum* L., and hereinafter referred to by the variety name 'ANTHETAAD'. The new *Anthurium* plant is a product of a planned breeding program conducted by the inventor in Bleiswijk, the Netherlands. The objective of this breeding program was to create a new plant with a height of 40.0 cm to 45.0 cm having shiny and blistered, red, oblong-cordate, and very durable spathes.

The new variety originated from a cross-pollination made in July 2008 in Bleiswijk, the Netherlands. The female parent was a pink *Anthurium* pot plant designated '8417-01' (unpatented), and the male parent was a red *Anthurium* pot plant designated '11985-01' (unpatented).

A single plant was selected from the progeny of the stated cross in July 2010. Asexual reproduction of the new variety by tissue culture in 2012 in Bleiswijk, the Netherlands, has demonstrated that the new variety reproduces true to type with all of the characteristics, as herein described, firmly fixed and retained through successive generations.

Community Plant Variety Rights for this variety have been applied for in the European Union on Nov. 27, 2017, by Applicant who obtained the subject matter disclosed directly from the inventor. 'ANTHETAAD' has not been made publicly available or sold anywhere in the world prior to the effective filing date of this application with the exception of sales or disclosures made one year or less before the effective filing date of this claimed invention by Applicant who obtained 'ANTHETAAD' directly from the inventor.

SUMMARY OF THE INVENTION

The following are the most outstanding and distinguishing characteristics of this new variety when grown under normal horticultural practices in Bleiswijk, the Netherlands:

1) Shiny and blistered, red, oblong-cordate spathes;
2) White spadices with yellow tips; and
3) Green, elliptical-cordate leaves.

DESCRIPTION OF THE PHOTOGRAPHS

This new *Anthurium* plant is illustrated by the accompanying photographs which show the overall plant habit including blooms and foliage of the plant; the colors shown are as true as can be reasonably obtained by conventional photographic procedures. The photographs are of a 44-week-old plant grown in a greenhouse in Bleiswijk, the Netherlands, in January 2020. Colors in the photographs may differ from the color values cited in the detailed botanical description, which accurately describe the actual colors of the new variety.

DESCRIPTION OF THE NEW VARIETY

Figure 1:
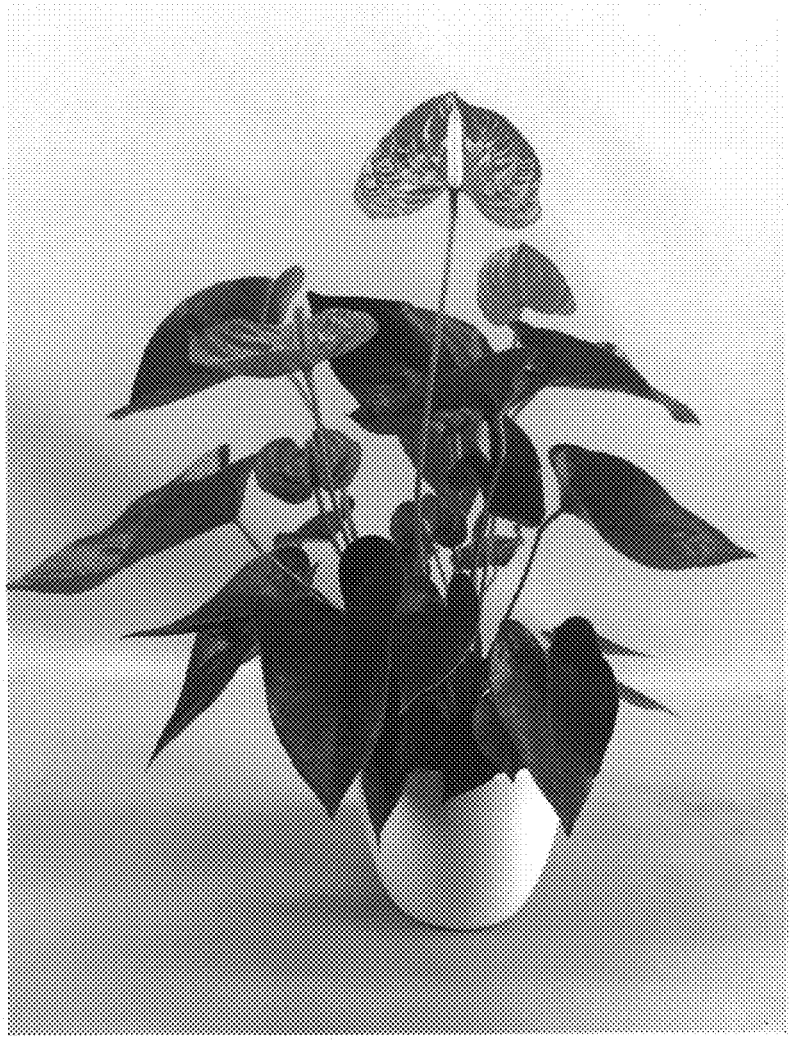
FIG. 1 shows the overall plant habit, including blooms and foliage.
Figure 2:
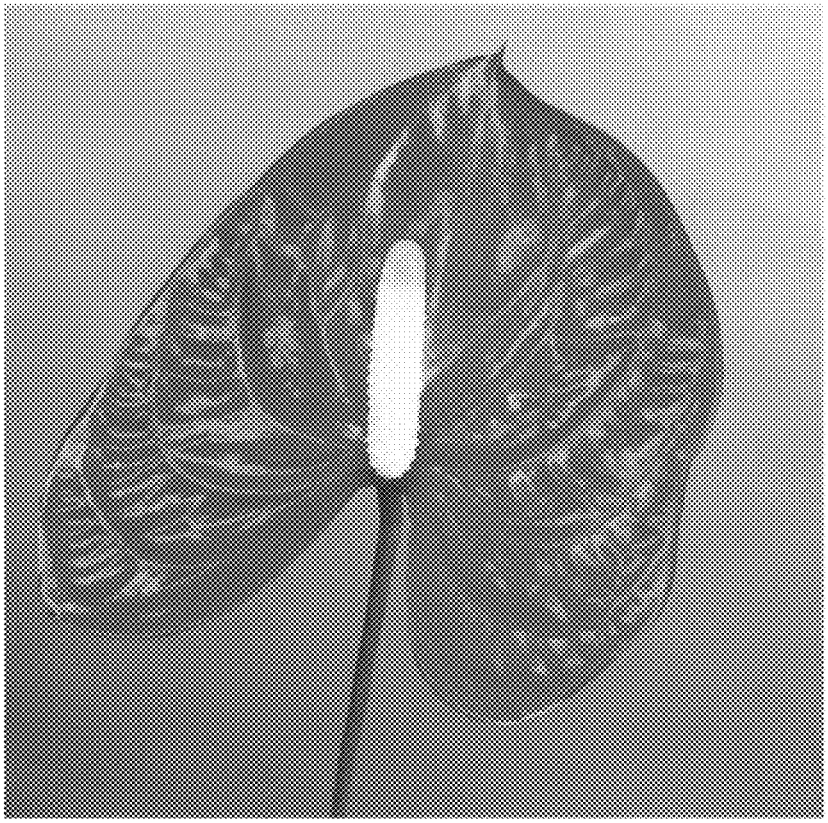
FIG. 2 shows a close-up of the mature spathe.
Figure 3:
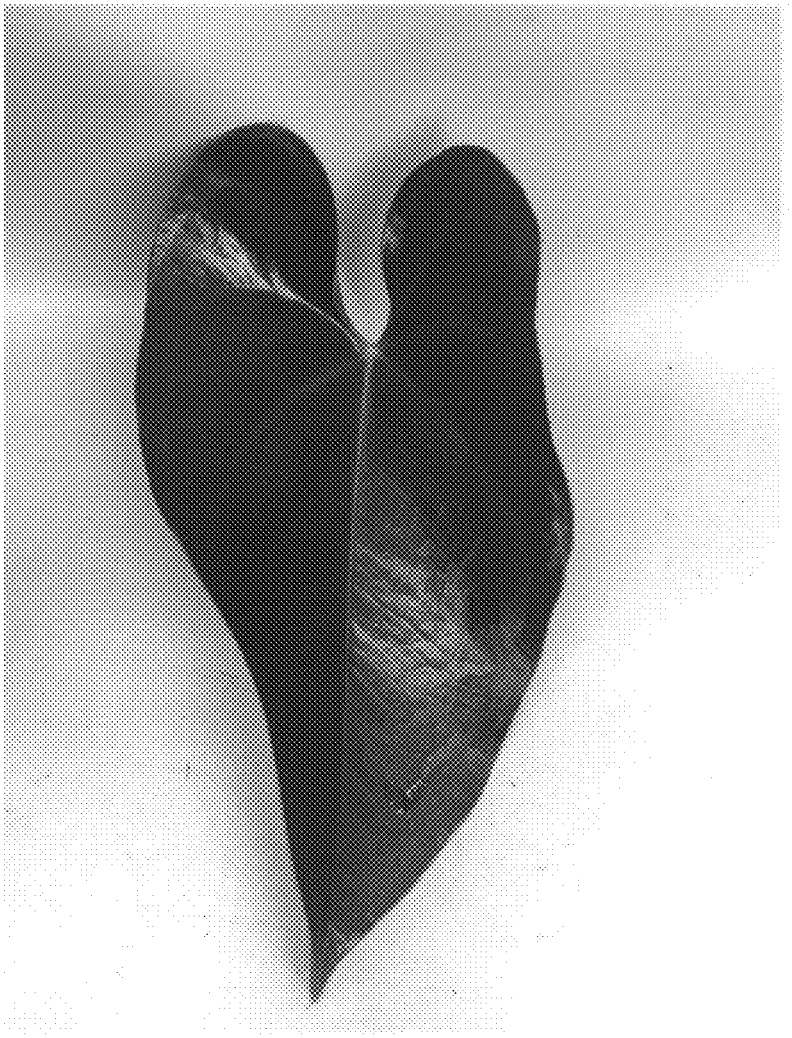
FIG. 3 shows a close-up of the upper leaf blade surface.

The following detailed description sets forth the distinctive characteristics of 'ANTHETAAD'. The data which define these characteristics were collected from asexual reproductions carried out in Bleiswijk, the Netherlands. The plant history was taken on 44-week-old plants which were planted from tissue culture in 14-centimeter (diameter) pots and grown in a glass greenhouse between 19° C. and 24° C. Observations were made in January 2020. Color readings were taken under 5000 lux natural light in the greenhouse. Color references are primarily to The R.H.S. Colour Chart of The Royal Horticultural Society of London (R.H.S.) (2015).

DETAILED BOTANICAL DESCRIPTION

Classification:

*Family*.—Araceae.

*Botanical*.—*Anthurium andraeanum* L.

*Common name*.—*Anthurium*.

*Denomination*.—'ANTHETAAD'.

Parentage:

*Female parent*.—*Anthurium* plant '8417-01' (unpatented).

*Male parent*.—*Anthurium* plant '11985-01' (unpatented).

Plant:

*Propagation*.—Tissue culture.

*Root description*.—Fleshy, creamy colored roots with small hairy lateral roots having yellow colored root tips.

*Time to produce a finished flowering plant*.—42 to 46 weeks after planting in a 14-cm (diameter) pot.

*Growth habit*.—Upright.

*Height* (*measured from soil, including inflorescence*).—40.0 cm to 45.0 cm.

*Width* (*measured from leaf tips*).—38.0 cm to 43.0 cm.

Leaves:

*Immature leaves*.—Length: 13.0 cm to 15.0 cm. Width: 8.0 cm to 9.0 cm. Color: Upper surface: RHS 146A. Lower surface: RHS 146B. Texture (both upper and lower surfaces): Leathery, soft, thin, and glossy.

*Mature leaves*.—Length (fully expanded): 18.0 cm to 20.0 cm. Width: 11.0 cm to 13.0 cm. Shape: Elliptical cordate. Apex: Acuminate. Base: Cordate. Leaf blade angle with the petiole: Between 100 degrees and 120 degrees. Leaf margin: Entire. Color: Upper surface: RHS 147A. Lower surface: RHS 146A. Texture: Upper surface: Leathery, thick, smooth, and matt. Lower surface: Leathery, thick, smooth, and glossy. Venation: Pinnate veining; the mid-vein and primary veins (the veins that radiate out from the junction of petiole and leaf) protrude at the underside of the leaf blade. Venation color: Upper surface: RHS 144A. Lower surface: RHS 144B.

*Lobes*.—Present. Arrangement: Leaf blade has two lobes extending past the petiole. The lobes are non-touching. Length of lobes of mature leaf blades: 3.0 cm to 4.0 cm. Width of lobes of mature leaf blades: 4.0 cm to 5.0 cm. Distance from petiole/leaf junction to highest point on lobes of mature leaf: 4.0 cm to 5.0 cm.

*Petiole*.—Cross-section: Round. Diameter: 0.3 cm to 0.4 cm. Length: 19.0 cm to 22.0 cm for a mature leaf size. Color: Mature leaf: RHS 144B. Immature leaf: RHS 144C. Cataphyll color surrounding the petiole: Outside: RHS 144C. Inside: RHS 144D.

*Geniculum*.—Length: 2.5 cm to 3.5 cm. Width: 0.4 cm to 0.5 cm. Color: RHS 144C.

Inflorescence:

*Arrangement*.—Single.

*Flowering habit* (*length of flowering season*).—Continuous.

*Number of inflorescences per plant*.—6 to 8.

*Fragrance*.—Absent.

*Longevity of inflorescence on plant*.—Over a year.

Spathe:

*Buds*.—The spathe is tightly rolled around the spadix and extrudes from the peduncle sheath. After the spathe is fully opened, the peduncle elongates some extra centimeters (average elongation is 2.0 cm to 5.0 cm).

*Arrangement*.—Spathe angle with the peduncle is between 110 degrees and 130 degrees; the spathe stands on a wiry peduncle about 7.0 cm to 10.0 cm above the foliage.

*Shape*.—Oblong cordate.

*Apex*.—Mucronate.

*Base*.—Cordate.

*Texture*.—Shiny and blistered.

*Margin*.—Undulated.

*Size*.—Length: 11.0 cm to 13.0 cm. Width: 10.5 cm to 11.5 cm.

*Lobes*.—Present. Arrangement: The spathe has two lobes extending past the peduncle. The lobes are non-touching. Length: 3.0 cm to 4.0 cm. Width: 4.5 cm to 5.5 cm.

*Color*.—Just fully open: Upper surface: RHS 45B. Lower surface: RHS 45D. This red color remains for a very long period, at least more than 30 weeks after opening.

Peduncle:

*Shape*.—Erect.

*Cross-section*.—Round.

*Length*.—33.0 cm to 36.0 cm.

*Diameter*.—0.4 cm to 0.5 cm.

*Color*.—RHS 145A.

Flowering time:

*General*.—One small, rooted, untreated tissue culture plant of 8.0 cm tall will flower, depending on the season, after 42 to 46 weeks and 6 to 7 blossoms appear. More blossoms appear after some additional weeks so that a full flowering and commercial plant will have 7 to 8 red spathes. Smaller blossoms may occur on immature plants.

Spadix:

*Size*.—Length: 3.5 cm to 4.5 cm (depending on flower size). Width (at apex): 0.6 cm to 0.7 cm. Width (at base): 0.7 cm to 0.8 cm.

*Shape*.—Columnar.

*Angle from spadix tip to peduncle*.—160 degrees to 170 degrees.

*Texture*.—When the spathe is unfurling the spadix is smooth. When the spadix matures, small stigmata protrude. The stigmata are evenly distributed around the spadix. The spadix matures from base to top, slowly giving the spadix a somewhat rough appearance.

*Color*.—Immature: RHS 155B. Mature: RHS 17A. Ages to: RHS 152C.

Flowers:

*Quantity per spadix*.—100 to 150.

*Spadix flower arrangement*.—Bisexual, rounded in cross-section.

*Shape*.—Rounded.

*Size*.—Length: 0.05 cm to 0.10 cm. Diameter (maximum): 0.10 cm.

*Color*.—RHS 156D.

Reproductive organs:

*Stamens*.—Not visible.

*Pollen amount*.—Absent.

*Pistil*.—Quantity: Many. Length: Less than 0.01 cm. Color: RHS 156D.

*Style*.—Not observed to date.

*Stigma*.—Shape: Ovoid. Diameter: Less than 0.01 cm. Color: RHS 156D.

*Ovary*.—Rarely visible.

*Ovary color*.—Not measured.

Fruit and seed set: None observed to date.

Disease and pest resistance: No specific resistance or susceptibility observed to pathogens or pests common to *Anthurium* under commercial conditions to date.

COMPARISON WITH PARENTAL AND SIMILAR COMMERCIAL VARIETIES

'ANTHETAAD' differs from the female parent plant '8417-01' (unpatented) in that 'ANTHETAAD' has red, oblong-cordate spathes in an upwards direction, whereas '8417-01' has pink, orbicular-cordate spathes in a horizontal direction.

'ANTHETAAD' differs from the male parent plant '11985-01' (unpatented) in that 'ANTHETAAD' has free (non-touching) spathe lobes, whereas '11985-01' has overlapping spathe lobes.

'ANTHETAAD' differs from similar commercial variety 'ANTHDASZUM' (U.S. Plant Pat. No. 29,721) in that 'ANTHETAAD' has green cataphylls, elliptical-cordate leaves, and undulated spathe margins, whereas 'ANTHDASZUM' has red-brown cataphylls, narrow long-cordate leaves, and entire spathe margins.

'ANTHETAAD' differs from similar commercial variety 'ANTHABUDON' (U.S. Plant Pat. No. 20,282) in that 'ANTHETAAD' has green cataphylls and undulated spathe margins, whereas 'ANTHABUDON' has purple-red cataphylls and entire spathe margins. Additionally, 'ANTHETAAD' has fewer flowers per spadix than 'ANTHABUDON'.

I claim:

1. A new and distinct variety of *Anthurium* plant named 'ANTHETAAD', substantially as illustrated and described herein.

* * * * *